United States Patent
Pahima et al.

(10) Patent No.: US 10,368,780 B2
(45) Date of Patent: Aug. 6, 2019

(54) BODY WORN ANTENNA

(71) Applicant: CHECK-CAP LTD., Isfiya (IL)

(72) Inventors: Yosi Pahima, Karmiel (IL); Maxim Kaplan, Karmiel (IL)

(73) Assignee: CHECK-CAP LTD., Isfiya (IL)

( * ) Notice: Subject to any disclaimer, the term of this patent is extended or adjusted under 35 U.S.C. 154(b) by 147 days.

(21) Appl. No.: 15/314,103

(22) PCT Filed: May 9, 2016

(86) PCT No.: PCT/IL2016/050489
§ 371 (c)(1),
(2) Date: Nov. 28, 2016

(87) PCT Pub. No.: WO2016/181388
PCT Pub. Date: Nov. 17, 2016

(65) Prior Publication Data
US 2017/0196480 A1    Jul. 13, 2017

Related U.S. Application Data

(60) Provisional application No. 62/159,288, filed on May 10, 2015.

(51) Int. Cl.
*H01Q 1/27* (2006.01)
*A61B 5/07* (2006.01)
(Continued)

(52) U.S. Cl.
CPC .......... *A61B 5/073* (2013.01); *A61B 1/00016* (2013.01); *A61B 1/041* (2013.01);
(Continued)

(58) Field of Classification Search
CPC ....... A61B 5/073; A61B 5/0031; A61B 6/425; A61B 1/041; H01Q 1/273; H01Q 1/276; H04B 1/385
See application file for complete search history.

(56) References Cited

U.S. PATENT DOCUMENTS 7,787,926 B2    8/2010    Kimchy
9,037,219 B2    5/2015    Baum et al.
(Continued)

FOREIGN PATENT DOCUMENTS

| CN | 202261179 | * | 5/2012 |
| EP | 2617346 A1 | | 7/2013 |
| WO | WO2009110679 | * | 9/2009 |

OTHER PUBLICATIONS

The American Radio Relay League. Gerald Hall. (Year: 1988).*
(Continued)

*Primary Examiner* — Hoang V Nguyen
*Assistant Examiner* — Awat M Salih
(74) *Attorney, Agent, or Firm* — Soroker Agmon Nordman

(57) ABSTRACT

A wearable antenna for communicating between an external transceiver and a capsule inside the gastrointestinal tract of a user, including a printed circuit board for forming a conducting pattern on a first face and on a second face of the printed circuit board; a first conducting pattern on the first face of the printed circuit board, including: a) an almost completely split conducting elongated bar across a center of the printed circuit board; b) an identical main conducting transmission area on each side of the almost completely split elongated bar; c) a thin conducting line respectively connecting between each side of the almost completely split elongated bar and the transmission area; a second conducting pattern on the second face of the printed circuit board including a U shaped conductor; wherein the U shaped conductor is positioned to serve as a balun for the conducting pattern on the first face.

18 Claims, 6 Drawing Sheets

(51) Int. Cl.
*A61B 6/00* (2006.01)
*A61B 5/06* (2006.01)
*H01Q 1/38* (2006.01)
*H01Q 9/28* (2006.01)
*A61B 1/00* (2006.01)
*A61B 1/04* (2006.01)

(52) U.S. Cl.
CPC ............ *A61B 5/062* (2013.01); *A61B 6/4057* (2013.01); *A61B 6/4258* (2013.01); *A61B 6/56* (2013.01); *H01Q 1/273* (2013.01); *H01Q 1/38* (2013.01); *H01Q 9/285* (2013.01); *A61B 5/066* (2013.01); *A61B 6/483* (2013.01); *A61B 6/485* (2013.01); *A61B 2562/166* (2013.01)

(56) References Cited

U.S. PATENT DOCUMENTS

| | | |
|---|---|---|
| 2006/0004285 A1 | 1/2006 | Meron et al. |
| 2008/0249360 A1 | 10/2008 | Li et al. |
| 2010/0130837 A1 | 5/2010 | Matott |
| 2010/0303200 A1 | 12/2010 | Kimchy et al. |
| 2011/0291769 A1 | 12/2011 | Dalmia et al. |
| 2012/0071710 A1 | 3/2012 | Gazdznski |
| 2013/0038493 A1 | 2/2013 | Druyan |
| 2013/0237809 A1 | 9/2013 | Hasegawa |
| 2014/0037069 A1 | 2/2014 | Kimchy et al. |
| 2016/0240933 A1* | 8/2016 | Wu .................... H01Q 21/26 |

OTHER PUBLICATIONS

Nemiroski. 2011. A Wireless Lab-in-a-Pill Biosensor for Rapid Detection of Gastrointestinal Bleeding. Harvard University Cambridge, Massachusetts.

El Hatmi Fatiha et al: "A Multilayered Coil Antenna for Ingestible Capsule: Near-Field Magnetic Induction Link", IEEE Antennas and Wireless Propagation Letters, vol. 12, Sep. 20, 2013, pp. 1118-1121.

Zhao Wang et al: "Review of the Wireless Capsule Transmitting and Receiving Antennas", In: "Wireless Communications and Networks—Recent Advances", Mar. 14, 2012.

* cited by examiner

BODY WORN ANTENNA

RELATED APPLICATIONS

This application claims priority under 35 U.S.C. 120 from U.S. provisional application No. 62/159,288 dated May 10, 2015, the disclosure of which is incorporated herein by reference.

FIELD OF THE DISCLOSURE

The present disclosure relates generally to an antenna that is worn on a person's body to communicate with a capsule that was swallowed by the person and is traveling through the gastrointestinal tract.

BACKGROUND OF THE DISCLOSURE

One method for examining the gastrointestinal tract for the existence of polyps and other clinically relevant features that may provide an indication regarding the potential of cancer is performed by swallowing an imaging capsule that travels through the gastrointestinal tract and views the patient's situation from within. In a typical case the trip can take between 24-48 hours, after which the imaging capsule exits in the patient's feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits X-rays and/or Gamma rays. The radiation typically may be collimated to allow it to be controllably directed toward a specific area during the imaging process. In an exemplary case the imaging capsule is designed to measure X-Ray fluorescence and/or Compton back-scattering and transmit the measurements (e.g. count rate, particle energy) to an external analysis device, for example an external transceiver worn by the patient and/or a computer or other dedicated instruments.

U.S. Pat. No. 7,787,926 dated Aug. 31, 2010 and U.S. Pat. No. 9,037,219 dated May 19, 2015 both by the current applicant, the disclosures of which are incorporated herein by reference, describe details related to the manufacture and use of such an imaging capsule.

It is desirable to minimize the amount of power required by the imaging capsule to successfully perform its trip through the gastrointestinal tract so that the size of a required power source can be reduced. Therefore it is desirable to optimize communications to reduce the amount of power required to communicate with the external transceiver.

SUMMARY OF THE DISCLOSURE

An aspect of an embodiment of the disclosure, relates to a wearable antenna that can be attached to the lower back of a user or placed at other locations on the user's body near the gastrointestinal tract of the user, for example near the colon and small intestine. The wearable antenna is designed to provide an electromagnetic radiation pattern that optimally covers the path of a capsule traversing the gastrointestinal tract. The wearable antenna is made from a two faced printed circuit board with a printed conducting pattern on both faces of the printed circuit board. On a first face there is printed an almost symmetrical pattern having a split elongated bar down the center of the printed circuit board and an identical main transmission area on either side of the split elongated bar to form a dipole transmission antenna. On each side of the split elongated bar a thin conducting line connects between a side of the split elongated bar and the main radiation area. On the second face there is printed an elongated bar approximately down the center of the printed circuit board to serve as a balun for the antenna. Optionally, the elongated bar on the second face is shifted right or left from the center to balance the transmission signal.

In an exemplary embodiment of the disclosure, the pattern of the conducting areas on the face of the antenna are designed to optimally serve as a transceiver antenna using an ISM band frequency (e.g. 433 Mhz) and taking into account the influence of the user's body being attached to the antenna.

There is thus provided according to an exemplary embodiment of the disclosure, a wearable antenna for communicating between an external transceiver and a capsule inside the gastrointestinal tract of a user, comprising:
  a printed circuit board for forming a conducting pattern on a first face and on a second face of the printed circuit board;
  a first conducting pattern on the first face of the printed circuit board, comprising:
    a) an almost completely split conducting elongated bar across a center of the printed circuit board forming a void between each side of the almost completely split elongated bar;
    b) an identical main conducting transmission area on each side of the almost completely split elongated bar;
    c) a thin conducting line respectively connecting between each side of the almost completely split elongated bar and the transmission area;
  a second conducting pattern on the second face of the printed circuit board comprising a U shaped conductor having an elongated conducting area and an elongated conducting line; wherein the U shaped conductor is positioned to serve as a balun for the conducting pattern on the first face; and
  wherein the size of the printed circuit board is selected to be attachable to the lower back of the user and to transmit a signal having an ISM band frequency.

In an exemplary embodiment of the disclosure, the U shaped conductor on the second face of the printed circuit board is positioned with an offset relative to the center of the printed circuit board to balance the signal transmitted by the wearable antenna. Optionally, the U shaped conductor on the second face of the printed circuit board is shorted with the almost completely split conducting elongated bar on the first face of the printed circuit board. In an exemplary embodiment of the disclosure, the U shaped conductor is shorted with the almost completely split conducting elongated bar by via holes through the printed circuit board. Alternatively, the U shaped conductor is shorted with the almost completely split conducting elongated bar by an electrical connection along the external width of the printed circuit board. In an exemplary embodiment of the disclosure, the antenna is connected with a cable to an external transceiver located near the waist of the user. Optionally, the almost completely split conducting bar is larger than the main conducting transmission areas together. In an exemplary embodiment of the disclosure, the main conducting transmission areas together are larger than the almost completely split conducting bar. Optionally, one side of the almost completely split elongated bar includes an elongated line extending inward next to the void. In an exemplary embodiment of the disclosure, the elongated line has an identical or similar thickness as the elongated conducting line of the U shaped conductor.

There is further provided according to an exemplary embodiment of the disclosure, a method of communicating between an external transceiver and a capsule inside the gastrointestinal tract of a user, comprising:

attaching a wearable antenna to the body of the user wherein the wearable antenna includes a printed circuit board having a conducting pattern on a first face and on a second face of the printed circuit board;

preparing the printed circuit board by printing a first conducting pattern on the first face of the printed circuit board, comprising:
 a) an almost completely split conducting elongated bar across a center of the printed circuit board forming a void between each side of the almost completely split elongated bar;
 b) an identical main conducting transmission area on each side of the almost completely split elongated bar;
 c) a thin conducting line respectively connecting between each side of the almost completely split elongated bar and the transmission area;

preparing the printed circuit board by further printing a second conducting pattern on the second face of the printed circuit board comprising a U shaped conductor having an elongated conducting area and an elongated conducting line; wherein the U shaped conductor is positioned to serve as a balun for the conducting pattern on the first face; and wherein the size of the printed circuit board is selected to be attachable to the lower back of the user and to transmit a signal having an ISM band frequency.

In an exemplary embodiment of the disclosure, the U shaped conductor on the second face of the printed circuit board is positioned with an offset relative to the center of the printed circuit board to balance the signal transmitted by the wearable antenna. Optionally, the U shaped conductor on the second face of the printed circuit board is shorted with the almost completely split conducting elongated bar on the first face of the printed circuit board. In an exemplary embodiment of the disclosure, the U shaped conductor is shorted with the almost completely split conducting elongated bar by via holes through the printed circuit board. Alternatively, the U shaped conductor is shorted with the almost completely split conducting elongated bar by an electrical connection along the external width of the printed circuit board. In an exemplary embodiment of the disclosure, the antenna is connected with a cable to an external transceiver located near the waist of the user. Optionally, the almost completely split conducting bar is larger than the main conducting transmission areas together. In an exemplary embodiment of the disclosure, the main conducting transmission areas together are larger than the almost completely split conducting bar. Optionally, one side of the almost completely split elongated bar includes an elongated line extending inward next to the void. In an exemplary embodiment of the disclosure, the elongated line has an identical or similar thickness as the elongated conducting line of the U shaped conductor.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
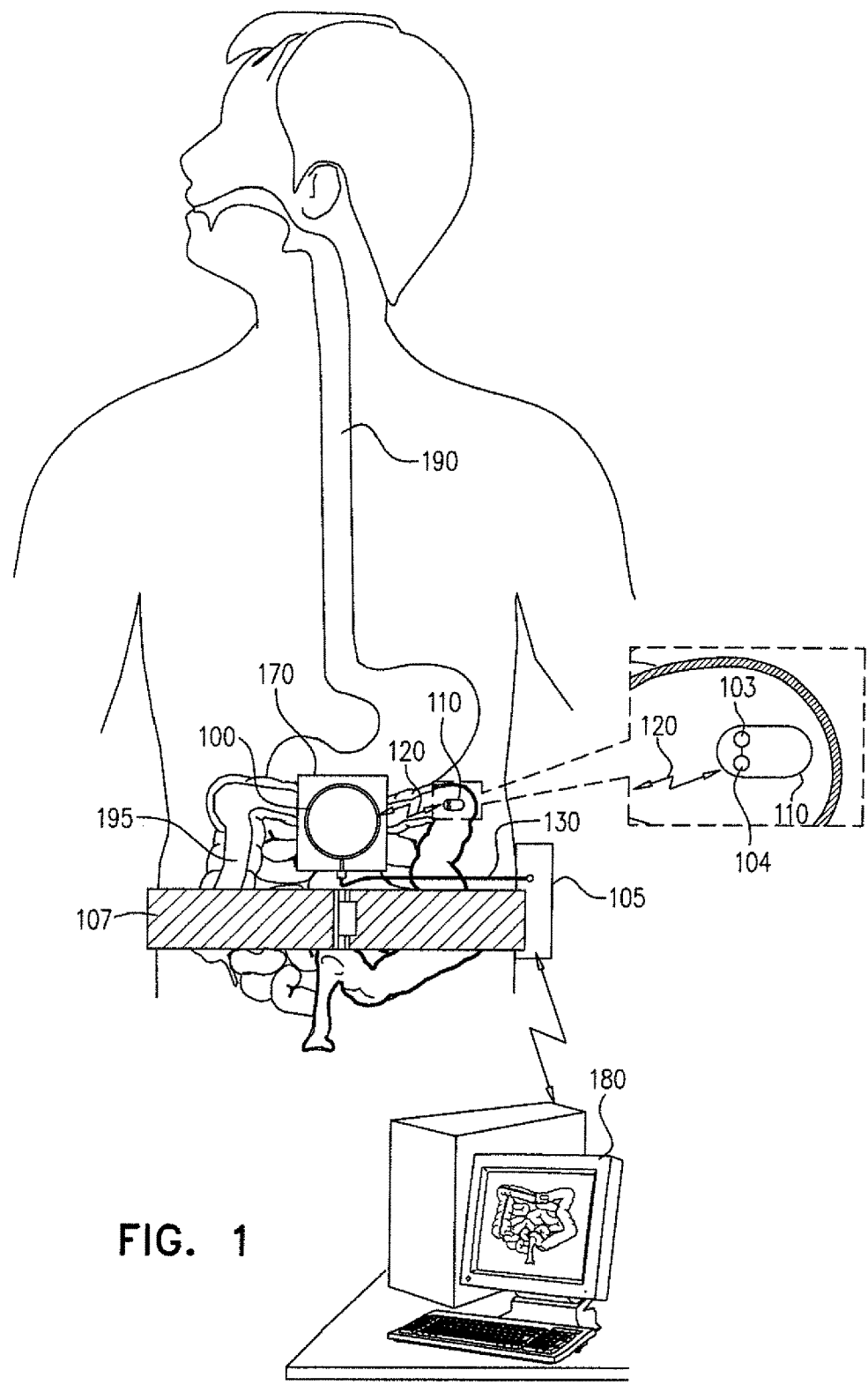
FIG. 1 is a schematic illustration of a wearable antenna deployed on a user, according to an exemplary embodiment of the disclosure.

FIG. 1 is a schematic illustration of a wearable antenna 100 deployed on a user, according to an exemplary embodiment of the disclosure. In an exemplary embodiment of the disclosure, the user swallows a capsule 110 to examine the gastrointestinal tract 190 and especially the colon 195. Optionally, the capsule 110 includes a power source 103 and transceiver 104 for communicating with an external transceiver 105 that may be deployed around the user's waist, for example on a belt 107. In an exemplary embodiment of the disclosure, the wearable antenna 100 is attached to the user's body, for example adhesively attached to the user's lower back or lower part of the stomach to transmit and receive signals 120 communicated between the capsule 110 (e.g. when located in the colon 195 or small intestine) and the external transceiver 105. Optionally, the wearable antenna 100 may be taped to the body of the user, for example with a two sided tape or with a piece of tape 170 that is larger than the wearable antenna 100. In an exemplary embodiment of the disclosure, the wearable antenna 100 is connected to the external transceiver 105 with a cable 130 (e.g. coaxial cable) for providing a signal 120 to the wearable antenna 100 and/or receiving a signal 120. In some embodiments of the disclosure, external transceiver 105 may communicate with a computer 180 to assist in analyzing information received from the capsule 110. Optionally, the capsule 110 may record images, deliver medication and/or perform other actions as known in the art.

Figure 2:
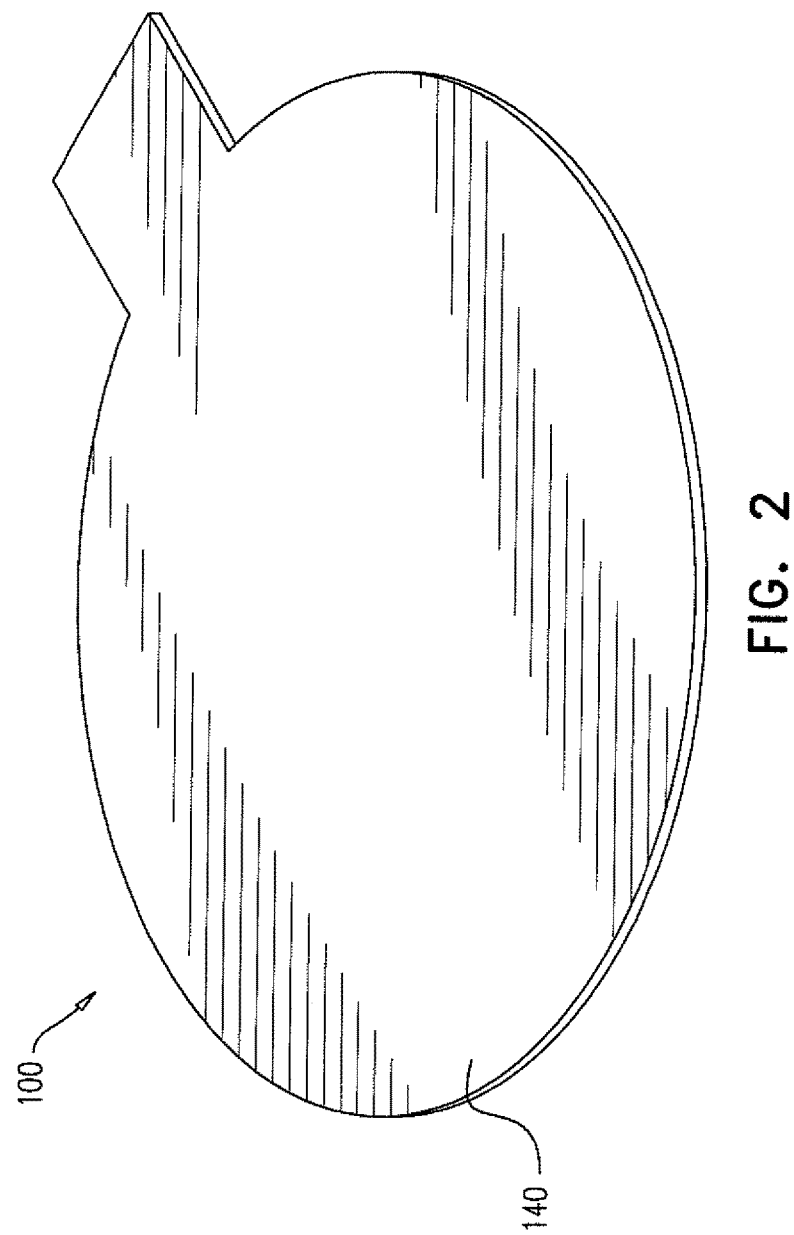
FIG. 2 is a schematic illustration of a wearable antenna, according to an exemplary embodiment of the disclosure.

FIG. 2 is a schematic illustration of wearable antenna 100, according to an exemplary embodiment of the disclosure. In an exemplary embodiment of the disclosure, the wearable antenna 100 is designed to optimally communicate with the capsule 110. Optionally, the wearable antenna 100 is essentially shaped as a circle with a radius of about 20-40 mm. In an exemplary embodiment of the disclosure, the wearable antenna 100 is formed by printing a conducting layer on a first face and a second face of an electrically isolated printed circuit board (PCB) 140. Optionally, the printed circuit board 140 may be rigid or alternatively it may be elastic so that it can bend with the curvature of the user's body when deployed on the user's body. In an exemplary embodiment of the disclosure, the printed circuit board 140 is made from a flame retardant (FR) material such as FR-4, which is made from a glass reinforced epoxy laminate sheet. Optionally, the width of the circuit board is between 0.1 mm to 1.0 mm, for example 0.254 mm (10 milli-inches).

Figure 3A:
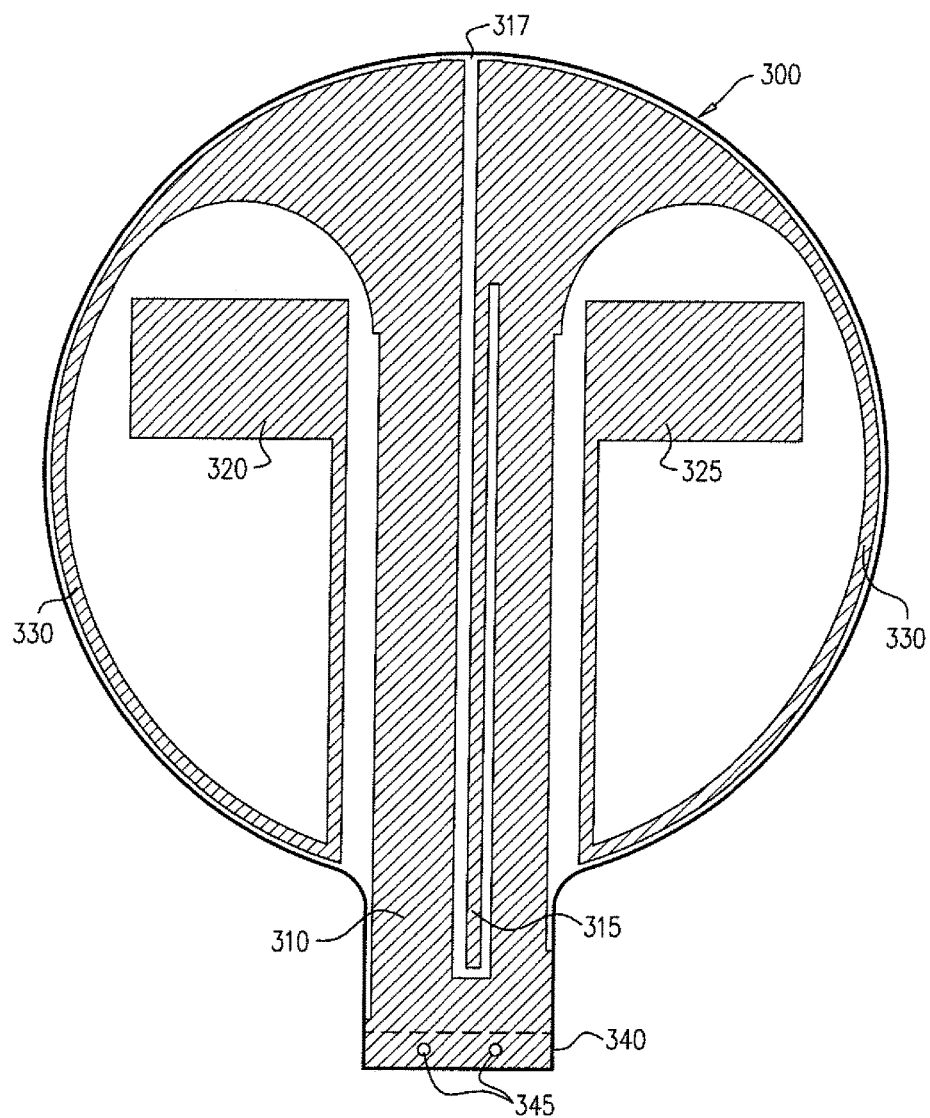
FIG. 3A is a schematic illustration of a conducting layer printed on a first face of the wearable antenna, according to an exemplary embodiment of the disclosure.
Figure 3B:
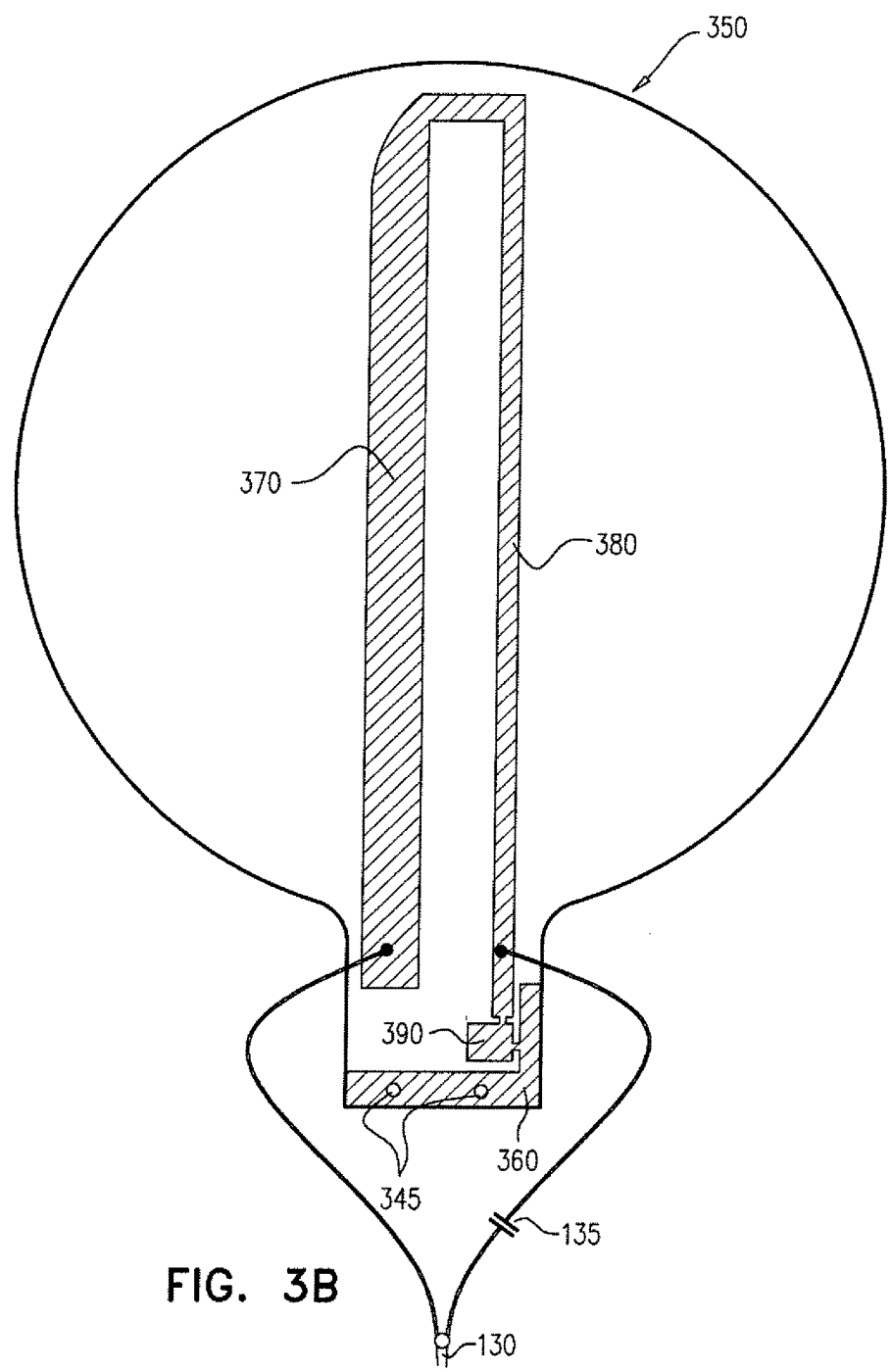
FIG. 3B is a schematic illustration of a conducting layer printed on a second face of the wearable antenna, according to an exemplary embodiment of the disclosure.

FIG. 3A is a schematic illustration of a conducting layer 300 printed on a first face of the wearable antenna 100, and FIG. 3B is a schematic illustration of a conducting layer 350 printed on a second face of the wearable antenna 100, according to an exemplary embodiment of the disclosure. In an exemplary embodiment of the disclosure, the conducting layer 300 on the first face of the printed circuit board 140 is designed as a planar dipole antenna having an almost completely split central elongated bar area 310 with each side of the elongated bar area 310 connected by a thin conducting line 330 to one of two main transmission areas 320, 325. In an exemplary embodiment of the disclosure, the split in the middle of elongated bar area 310 forms a void 317 serving as an induction split between both sides of the elongated bar area 310. Optionally, the transmission area (320, 325) are positioned symmetrically on opposite sides of the elongated bar area 310 and the transmission areas (320, 325) are shaped as solid conducting shaped areas of similar shape and size to form a dipole signal based on two identical slightly phase shifted radiating electromagnetic signals. In some embodiments of the disclosure, the solid conducting shaped areas are rectangular. Alternatively, the transmission areas may have other identical shapes, such as triangles, ellipses, circles, trapezoids or squares. In some embodiments of the disclosure, the main transmission areas (320, 325) together are larger than the elongate bar area 310 to enhance the dipole transmission. Alternatively, the elongated bar area 310 is larger than the area of the main transmission areas to provide a stronger offset for the dipole radiation signal. In some embodiments of the disclosure, one side of the elongated bar area 310 includes an elongated line 315 extending inward from the elongated bar area 310 next to void 317. Optionally, the elongated line 315 is thinner than the elongated bar area 310.

In an exemplary embodiment of the disclosure, the conducting layer 350 on the second face of the printed circuit board 140 includes a U shaped conducting area to serve as a balun for wearable antenna 100. In an exemplary embodiment of the disclosure, the U shaped conducting area includes an elongated conducting area 370 and an elongated conducting line 380 that control the inductive coupling with conducting layer 300 and it various parts (e.g. 310, 315, 320, 325, 330, and 340).

Optionally, the elongated conducting area 370 is thicker than the elongated conducting line 380. In an exemplary embodiment of the disclosure, the elongated conducting area 370 and/or the elongated conducting line 380 are slightly shifted off from the center to the sides by a predetermined amount to control the influence of the balun in balancing the radiation signals of the wearable antenna 100. Optionally, the elongated conducting area 370 and the elongated conducting line 380 are isolated from the conducting layer 300 printed on a first face of the wearable antenna 100. Alternatively, the elongated conducting area 370 and the elongated conducting line 380 are electrically connected to the printed layer on the first face by a base area 360 on the second face that is connected to a base area 340 on the first face, for example the two faces being connected along the external width of the printed circuit board 140 or through via holes 345 between base area 340 and base area 360. In some embodiments of the disclosure, a connection block 390 serves as a mediator between elongated conducting line 380 and base area 360. Optionally, the elongated conducting line 380 may be electrically disconnected from base area 360 or may be electrically connected. In some embodiments of the disclosure, connection block 390 may include a capacitor or inductor to control the connection with base 360. In some embodiments of the disclosure, cable 130 is connected from transceiver 105 to elongated conducting area 370 and elongated conducting line 380, for example cable 130 may be a coax cable with the core connected to elongated conducting line 380 and the ground connected to elongated conducting area 370. Optionally the line may include capacitors 135 or inductors to control the signals handled by the wearable antenna 100.

In some embodiments of the disclosure, the thickness of elongated conducting line 380 is similar or identical to the thickness of elongated line 315

In an exemplary embodiment of the disclosure, the antenna is configured to communicate with the capsule 110 using an ISM radio band signal to fit international regulations, for example a 433 Mhz signal and having a 10 Mhz bandwidth. Optionally, wearable antenna 100 is designed to have a single ended (unbalanced) impedance, for example of about 50 Ohm when positioned in the proximity of the body of a user (e.g. taking into account the dielectric properties of the body of the user).

In an exemplary embodiment of the disclosure, the design of wearable antenna 100 is optimally tuned empirically so that it generates an almost uniform omnidirectional 3D radiation pattern when deployed near the body of the user. Optionally, wearable antenna 100 also provides an enhanced power gain in contrast to other antennas of similar size when transmitting with ISM frequencies near a user's body.

Figure 4:
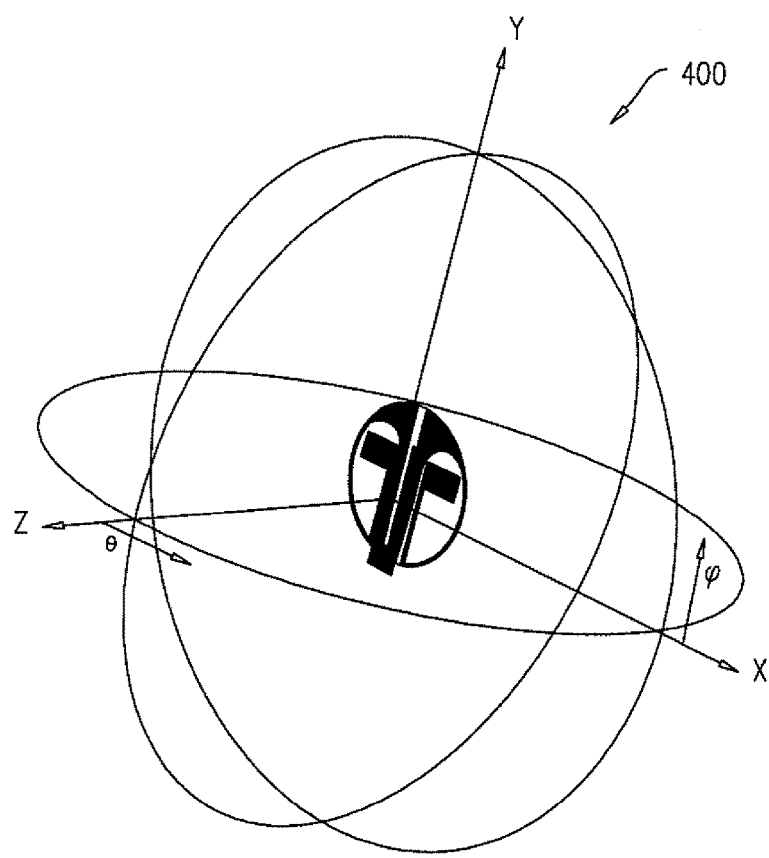
FIG. 4 is a schematic illustration of a 3 dimensional radiation pattern using the wearable antenna, according to an exemplary embodiment of the disclosure.
Figure 5:
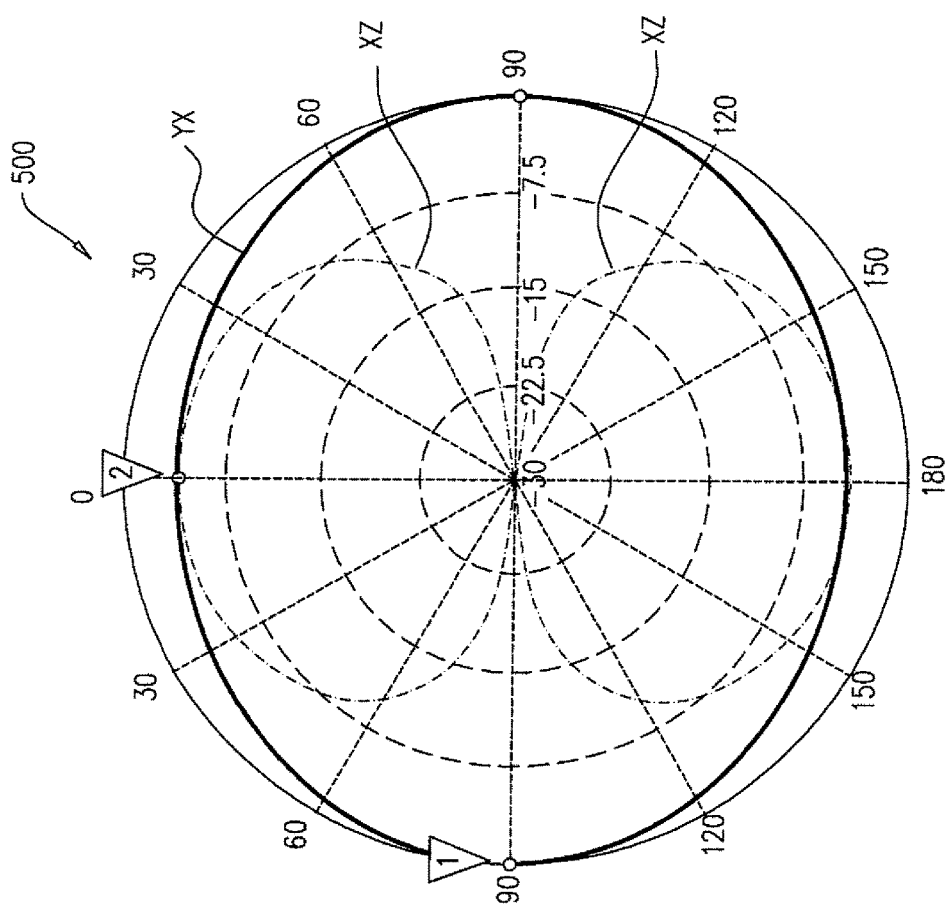
FIG. 5 is a schematic illustration of power gain versus angle using the wearable antenna, according to an exemplary embodiment of the disclosure.

FIG. 4 is a schematic graph 400 of a 3 dimensional radiation pattern 400 using the wearable antenna, and FIG. 5 is a schematic graph 500 of power gain versus angle using the wearable antenna, according to an exemplary embodiment of the disclosure.

As shown by graph 400 and graph 500 the signal provided by wearable antenna 100 spreads out evenly to cover the surroundings of the wearable antenna, thus providing a good connection with capsule 110 especially after leaving the stomach and reaching the small intestine and colon.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure.

It will be appreciated by persons skilled in the art that the present invention is not limited to what has been particularly shown and described hereinabove. Rather the scope of the present invention is defined only by the claims, which follow.

We claim:

1. A wearable antenna for communicating between an external transceiver and a capsule inside the gastrointestinal tract of a user comprising:

a printed circuit board comprising a first continuous planar conducting pattern printed directly on a first face and a second continuous planar conducting pattern printed directly on a second face of the printed circuit board, the first conducting pattern on the first face of the printed circuit board, comprising:

a) a conducting elongated bar across a center of the printed circuit board: wherein the elongated bar is partially split to form two sides, forming a void between the sides of the elongated bar:

b) an identical main conducting transmission area on each side of the elongated bar:

c) a thin conducting line respectively connecting between each side of the elongated bar and the transmission area:
the second conducting pattern on the second face of the printed circuit board comprising:
a U shaped conductor having an elongated conducting area and an elongated conducting line: wherein the U shaped conductor is positioned to serve as a balun for the conducting pattern on the first face; and
wherein the size of the printed circuit board is selected to be attachable to the lower back of the user and to transmit a signal having an ISM band frequency, wherein the U shaped conductor is shorted with the conducting elongated bar by via holes through the printed circuit board.

2. A wearable antenna according to claim 1, wherein the U shaped conductor on the second face of the printed circuit board is positioned with an offset relative to the center of the printed circuit board to balance the signal transmitted by the wearable antenna.

3. A wearable antenna according to claim 1, wherein the U shaped conductor is shorted with the conducting elongated bar by an electrical connection along an external width of the printed circuit board.

4. A wearable antenna according to claim 1, wherein the antenna is connected with a cable to the external transceiver located near the waist of the user.

5. A wearable antenna according to claim 1, wherein the conducting bar is larger than the main conducting transmission areas together.

6. A wearable antenna according to claim 1, wherein the main conducting transmission areas together are larger than the conducting bar.

7. A wearable antenna according to claim 1, wherein one side of the elongated bar includes an elongated line extending inward next to the void.

8. A wearable antenna according to claim 7, wherein the elongated line has an identical or similar thickness as the elongated conducting line of the U shaped conductor.

9. A method of communicating between an external transceiver and a capsule inside the gastrointestinal tract of a user, comprising:
attaching a wearable antenna to the body of the user wherein the wearable antenna includes a printed circuit board comprising a first continuous planar conducting pattern printed directly on a first face and a second continuous planar conducting pattern printed directly on a second face of the printed circuit board,
preparing the printed circuit board by printing the first conducting pattern on the first face of the printed circuit board, comprising:
a) a conducting elongated bar across a center of the printed circuit board: wherein the elongated bar is partially split to form two sides, forming a void between the sides of the elongated bar:
b) an identical main conducting transmission area on each side of the elongated bar:
c) a thin conducting line respectively connecting between each side of the elongated bar and the transmission area:
preparing the printed circuit board by further printing the second conducting pattern on the second face of the printed circuit board comprising a U shaped conductor having an elongated conducting area and an elongated conducting line: wherein the U shaped conductor is positioned to serve as a balun for the conducting pattern on the first face: and
wherein the size of the printed circuit board is selected to be attachable to the lower back of the user and to transmit a signal having an ISM band frequency, wherein the U shaped conductor is shorted with the conducting elongated bar by via holes through the printed circuit board.

10. A method according to claim 9, wherein the U shaped conductor on the second face of the printed circuit board is positioned with an offset relative to the center of the printed circuit board to balance the signal transmitted by the wearable antenna.

11. A method according to claim 9, wherein the U shaped conductor is shorted with the conducting elongated bar by an electrical connection along an external width of the printed circuit board.

12. A method according to claim 9, wherein the antenna is connected with a cable to the external transceiver located near the waist of the user.

13. A method according to claim 9, wherein the conducting bar is larger than the main conducting transmission areas together.

14. A method according to claim 9, wherein the main conducting transmission areas together are larger than the conducting bar.

15. A method according to claim 9, wherein one side of the elongated bar includes an elongated line extending inward next to the void.

16. A method according to claim 15, wherein the elongated line has an identical or similar thickness as the elongated conducting line of the U shaped conductor.

17. A wearable antenna for communicating between an external transceiver and a capsule inside the gastrointestinal tract of a user comprising:
a printed circuit board comprising a first continuous planar conducting pattern printed directly on a first face and a second continuous planar conducting pattern printed directly on a second face of the printed circuit board,
the first conducting pattern on the first face of the printed circuit board, comprising:
a) a conducting elongated bar across a center of the printed circuit board: wherein the elongated bar is partially split to form two sides, forming a void between the sides of the elongated bar:
b) an identical main conducting transmission area on each side of the elongated bar:
c) a thin conducting line respectively connecting between each side of the elongated bar and the transmission area:
the second conducting pattern on the second face of the printed circuit board comprising:
a U shaped conductor having an elongated conducting area and an elongated conducting line: wherein the U shaped conductor is positioned to serve as a balun for the conducting pattern on the first face;
wherein the size of the printed circuit board is selected to be attachable to the lower back of the user and to transmit a signal having an ISM band frequency, and wherein the thin conducting line is at least partially printed along an outline of the printed circuit board and together with the elongated bar completely surround the transmission area.

18. A method of communicating between an external transceiver and a capsule inside the gastrointestinal tract of a user, comprising:
attaching a wearable antenna to the body of the user wherein the wearable antenna includes a printed circuit board comprising a first continuous planar conducting pattern printed directly on a first face and a second continuous planar conducting pattern printed directly on a second face of the printed circuit board, preparing the printed circuit board by printing the first conducting pattern on the first face of the printed circuit board, comprising:

a) a conducting elongated bar across a center of the printed circuit board: wherein the elongated bar is partially split to form two sides, forming a void between the sides of the elongated bar:

b) an identical main conducting transmission area on each side of the elongated bar:

c) a thin conducting line respectively connecting between each side of the elongated bar and the transmission area:

preparing the printed circuit board by further printing the second conducting pattern on the second face of the printed circuit board comprising a U shaped conductor having an elongated conducting area and an elongated conducting line: wherein the U shaped conductor is positioned to serve as a balun for the conducting pattern on the first face:

wherein the size of the printed circuit board is selected to be attachable to the lower back of the user and to transmit a signal having an ISM band frequency, and wherein the thin conducting line is at least partially printed along an outline of the printed circuit board and together with the elongated bar completely surround the transmission area.

* * * * *